United States Patent
Takeguchi et al.

(10) Patent No.: US 9,752,214 B2
(45) Date of Patent: Sep. 5, 2017

(54) TITANIUM ALLOY

(75) Inventors: Shunsuke Takeguchi, Saitama (JP); Yoshiki Ishikawa, Saitama (JP); Takasumi Kubo, Saitama (JP); Shin Ishida, Saitama (JP); Hiroki Takahashi, Saitama (JP); Masafumi Morita, Saitama (JP); Masahito Miki, Saitama (JP)

(73) Assignees: NIPPON PISTON RING CO., LTD., Saitama (JP); NATIONAL UNIVERSITY CORPORATION SAITAMA UNIVERSITY, Saitama (JP)

( * ) Notice: Subject to any disclaimer, the term of this patent is extended or adjusted under 35 U.S.C. 154(b) by 55 days.

(21) Appl. No.: 13/983,005

(22) PCT Filed: Jan. 31, 2012

(86) PCT No.: PCT/JP2012/052143
§ 371 (c)(1),
(2), (4) Date: Jul. 31, 2013

(87) PCT Pub. No.: WO2012/105557
PCT Pub. Date: Aug. 9, 2012

(65) Prior Publication Data
US 2013/0309518 A1 Nov. 21, 2013

(30) Foreign Application Priority Data
Jan. 31, 2011 (JP) .................. 2011-018649

(51) Int. Cl.
*C22C 14/00* (2006.01)
*C22F 1/18* (2006.01)
(Continued)

(52) U.S. Cl.
CPC .............. *C22C 14/00* (2013.01); *A61L 27/06* (2013.01); *A61L 31/022* (2013.01); *C22C 27/02* (2013.01); *C22F 1/183* (2013.01); *Y10T 428/12* (2015.01)

(58) Field of Classification Search
CPC ......... C22C 14/00; C22C 27/02; C22C 30/00; C22F 1/183; A61L 27/06
See application file for complete search history.

(56) References Cited

U.S. PATENT DOCUMENTS 6,607,693 B1 * 8/2003 Saito ................... C22C 1/045
148/421
6,767,418 B1 * 7/2004 Zhang ................ A61L 27/06
148/421
(Continued)

FOREIGN PATENT DOCUMENTS

JP 2001-329325 A 11/2001
JP 2006-89826 A 4/2006
(Continued)

*Primary Examiner* — Scott Kastler
*Assistant Examiner* — Vanessa Luk
(74) *Attorney, Agent, or Firm* — Porzio, Bromberg Newman P.C.

(57) ABSTRACT

A titanium alloy includes 15 to 27 atomic % (at %) of tantalum (Ta) and 0 to 8 at % of tin (Sn), the balance being titanium (Ti) and unavoidable impurities, when the entire amount of the titanium alloy is taken as 100 at %. Therefore, the titanium alloy provided has characteristics suitable for medical device materials, biocompatible materials, etc.

8 Claims, 21 Drawing Sheets

(51) Int. Cl.
 *A61L 27/06* (2006.01)
 *A61L 31/02* (2006.01)
 *C22C 27/02* (2006.01)

(56) References Cited

U.S. PATENT DOCUMENTS

| | | | |
|---|---|---|---|
| 6,786,984 B1 | | 9/2004 | Hanada et al. |
| 7,261,782 B2 | * | 8/2007 | Hwang .................... C22F 1/183 |
| | | | 148/421 |
| 2002/0033717 A1 | * | 3/2002 | Matsuo ............................ 327/94 |
| 2009/0220811 A1 | | 9/2009 | Miyazaki et al. |

FOREIGN PATENT DOCUMENTS

| | | |
|---|---|---|
| JP | 2008-32183 A | 2/2008 |
| JP | 4302604 B2 | 7/2009 |
| WO | 2007-108178 A | 9/2007 |
| WO | 2008-016010 A1 | 2/2008 |

\* cited by examiner

| SAMPLE NO. | Ta (at%) | Sn (at%) | Ti+ UNAVOIDABLE IMPURITIES | FINAL HEAT TREAT-MENT TEMPERATURE (°C) |
|---|---|---|---|---|
| T1 | 19 | 4.5 | BALANCE | 25 (NO HEAT TREATMENT) ~750 |
| T2 | 23 | 1.5 | BALANCE | 25 (NO HEAT TREATMENT) ~750 |
| T3 | 23 | 3.0 | BALANCE | 25 (NO HEAT TREATMENT) ~750 |
| T4 | 23 | 4.5 | BALANCE | 25 (NO HEAT TREATMENT) ~750 |
| T5 | 27 | 1.5 | BALANCE | 25 (NO HEAT TREATMENT) ~750 |
| T6 | 27 | 3.0 | BALANCE | 25 (NO HEAT TREATMENT) ~750 |
| T7 | 27 | 4.5 | BALANCE | 25 (NO HEAT TREATMENT) ~750 |

| SAMPLE NO. | HEAT TREATMENT TEMPERATURE (°C) | TENSILE STRENGTH (Mpa) | YOUNG'S MODULUS (Gpa) | ELASTIC LIMIT (%) |
|---|---|---|---|---|
| T1 | 25 | 881.0 | 39.5 | 2.38 |
|  | 250 | 808.7 | 41.6 | 3.81 |
|  | 350 | 992.8 | 43.0 | – |
|  | 450 | 1184.1 | 46.5 | 3.29 |
|  | 550 | 1026.2 | 39.0 | – |
|  | 650 | 727.2 | 35.7 | 2.10 |
|  | 750 | 663.8 | 33.3 | – |
| T2 | 25 | 909.3 | 38.4 | 2.47 |
|  | 250 | 960.0 | 42.5 | 3.30 |
|  | 350 | 1085.5 | 42.8 | – |
|  | 450 | 1384.3 | 50.0 | 3.19 |
|  | 550 | 1246.2 | 52.6 | – |
|  | 650 | 716.5 | 55.6 | 1.68 |
|  | 750 | 705.1 | 50.0 | – |
| T3 | 25 | 941.1 | 33.5 | 2.59 |
|  | 250 | 1021.8 | 32.8 | 3.04 |
|  | 350 | 1162.8 | 34.9 | – |
|  | 450 | 1340.0 | 43.9 | 3.35 |
|  | 550 | 1029.0 | 39.9 | – |
|  | 650 | 743.3 | 35.8 | 1.87 |
|  | 750 | 768.5 | 36.3 | – |
| T4 | 25 | 889.2 | 34.9 | 2.57 |
|  | 250 | 932.9 | 30.3 | 3.02 |
|  | 350 | 999.9 | 37.5 | – |
|  | 450 | 1174.6 | 38.5 | 3.46 |
|  | 550 | 991.0 | 43.1 | – |
|  | 650 | 800.5 | 34.7 | 3.42 |
|  | 750 | 779.4 | 42.4 | – |
| T5 | 25 | 844.6 | 35.4 | 2.25 |
|  | 250 | 907.2 | 32.0 | 2.23 |
|  | 350 | 1013.6 | 31.5 | – |
|  | 450 | 1202.1 | 32.8 | 2.72 |
|  | 550 | 941.2 | 50.0 | – |
|  | 650 | 723.9 | 39.7 | 2.15 |
|  | 750 | 719.1 | 46.2 | – |
| T6 | 25 | 840.2 | 34.0 | 2.58 |
|  | 250 | 855.6 | 29.0 | 2.89 |
|  | 350 | 929.7 | 30.2 | – |
|  | 450 | 1062.3 | 32.3 | 3.19 |
|  | 550 | 917.3 | 31.9 | – |
|  | 650 | 753.8 | 32.4 | 2.40 |
|  | 750 | 720.1 | 32.6 | – |
| T7 | 25 | 818.6 | 37.0 | 2.66 |
|  | 250 | 870.8 | 40.8 | 2.61 |
|  | 350 | 949.9 | 45.9 | – |
|  | 450 | 1069.6 | 39.5 | 2.93 |
|  | 550 | 1029.1 | 45.8 | – |
|  | 650 | 854.6 | 50.5 | 2.93 |
|  | 750 | 757.4 | 52.5 | – |

FIG. 22

TITANIUM ALLOY

CROSS REFERENCE TO RELATED APPLICATION

This is a National Stage of International Application No. PCT/JP2012/052143, filed Jan. 31, 2012, which claims the benefit of Application No. 2011-18649, filed in Japan on Jan. 31, 2011, the disclosures of which Applications are incorporated by reference herein.

Field

The present invention relates to a titanium alloy suitable for medical guidewires, medical stents and the like.

BACKGROUND

Conventionally, titanium (Ti)-nickel (Ni)-based alloys are widely known as alloy materials used for medical guidewires, medical stents and the like. However, in recent years, attention is given to titanium (Ti)-tantalum (Ta)-based alloys containing no Ni that may cause allergies in a living body.

For example, Japanese Patent No. 4302604 proposes a Ti—Ta-based alloy containing one or both of tantalum (Ta) and niobium (Nb) in prescribed amounts and further containing 1 to 20 mol % of zirconium (Zr) and 1 to 6 mol % of molybdenum (Mo), wherein the total amount of Ta, Nb, Zr, and Mo is 60 mol % or less with the balance being Ti and unavoidable impurities. This Ti—Ta-based alloy contains no Ni and is therefore highly safe for the human body. Other features of the alloy are that it has superelasticity and high cold workability and therefore has high productivity.

SUMMARY

Technical Problem

Meanwhile, medical devices (medical appliances) such as medical guidewires and stents come into direct contact with blood etc. in a living body and are therefore required to be highly safe for the living body. In addition, since such a medical device is inserted into a blood vessel etc. of the living body and moved along a complicated path, the medical device is required to have elasticity and a small diameter and also have appropriate stiffness.

However, with the conventional Ti—Ta-based titanium alloy, it is difficult to form a thin guidewire having a diameter of about several tens of micrometers because of a problem such as workability, and the safety for a living body is not always high.

The present invention has been made to solve the foregoing conventional problems, and it is an object to provide a titanium alloy having characteristics suitable for medical device materials, biocompatible materials, etc.

Solution to Problem

The present invention is a titanium alloy characterized by comprising 15 to 27 atomic % (at %) of tantalum (Ta) and 0 to 8 at % of tin (Sn) with the balance being titanium (Ti) and unavoidable impurities, when the entire amount of the titanium alloy is taken as 100 at %.

The present invention is also characterized in that, in the titanium alloy according to the above means, a value obtained by dividing a total atomic % of the tantalum and the tin by a total atomic % of the titanium and the unavoidable impurities is 0.17 to 0.54.

The present invention is also characterized in that, in the titanium alloy according to the above means, a saturation magnetic flux density in a B-H curve obtained by a VSM method is $5.0 \times 10^{-4}$ T (tesla) or lower when an intensity of a magnetic field is $4.0 \times 10^5$ A/m.

The present invention is also characterized in that, the titanium alloy according to the above means has an elastic deformation strain of 1.0% or larger.

The present invention is also characterized in that the titanium alloy according to the above means has a Young's modulus of 25 GPa to 85 GPa.

The present invention is also characterized in that the titanium alloy according to the above means has a tensile strength of 600 MPa to 1,600 MPa.

The present invention is also characterized in that, in the titanium alloy according to the above means, in a three-point bending test performed under measurement conditions in which a distance between two supporting members is 20 mm and a diameter d of a pointed end of each of the supporting members and a pressing member is 5 mm, when the pressing member presses the titanium alloy formed into a wire having a diameter φ of 0.5 mm to a pressing depth of 4 mm at a pressing rate of 1 mm/minute and then a load is released, an amount of recovery of the wire is 60% or higher.

The present invention is also characterized in that, in the titanium alloy according to the above means, a degree of cell injury when a metal ion concentration measured by ICP emission spectrometry is 64 ppm or less is less than 10%.

The present invention is also characterized in that the titanium alloy according to the above means is used for a medical guidewire, a medical delivery wire, a medical stent, a medical clip, an aneurysm embolization coil or a vein filter, or a dental cleanser, a dental reamer, a dental file or an orthodontic wire.

The present invention is also characterized in that the titanium alloy according to the above means has a maximum outer diameter of 0.005 mm to 1 mm.

Advantageous Effects of Invention

The titanium alloy of the present invention has excellent effects in that characteristics suitable for medical device materials, biocompatible materials, etc. can be obtained.

BRIEF DESCRIPTION OF DRAWINGS

FIG. 22 is a table showing the results of the tensile test, i.e., the values of tensile strength, Young's modulus, and elastic deformation strain (elastic limit), on TiTaSn example samples of sample Nos. T1 to T7 (final working rate: 76%).

DESCRIPTION OF EMBODIMENT

A titanium alloy according to an embodiment of the present invention will next be described.

<Overall Titanium Alloy>

The titanium alloy according to the present invention is a titanium alloy characterized by comprising 15 to 27 atomic % (at %) of tantalum (Ta) and 0 to 8 at % of tin (Sn) with the balance being titanium (Ti) and unavoidable impurities, when the entire amount of the titanium alloy is taken as 100 at %. No particular limitation is imposed on the content of titanium (Ti) in the balance, and it is sufficient that, among the constituent elements, titanium (Ti) be an element with the largest atomic ratio.

Titanium alloys are broadly classified into three types, an α-type titanium alloy in which the matrix phase is an α phase of hexagonal close-packed (HCP) crystals, a β-type titanium alloy in which the matrix phase is a β phase of body centered-cubic (BCC) crystals, and an α+β type titanium alloy in which the α phase of hexagonal close-packed (HCP) crystals and the β phase of body centered-cubic (BCC) crystals coexist. However, no particular limitation is imposed on the type of the titanium alloy according to the present invention.

<Tantalum (Ta)>

Tantalum (Ta) allows the titanium alloy to undergo thermoelastic martensitic transformation. Ta has the function of lowering the temperature of transformation from the β phase to the α phase to thereby stabilize the β phase at room temperature and the function of increasing the resistance to slip deformation (plastic deformation).

When the entire amount of the titanium alloy is taken as 100 atomic % (at %), the content of Ta is preferably 15 to 27 at %, more preferably 19 to 25 at %, and most preferably 22 to 24 at %.

Figure 1:
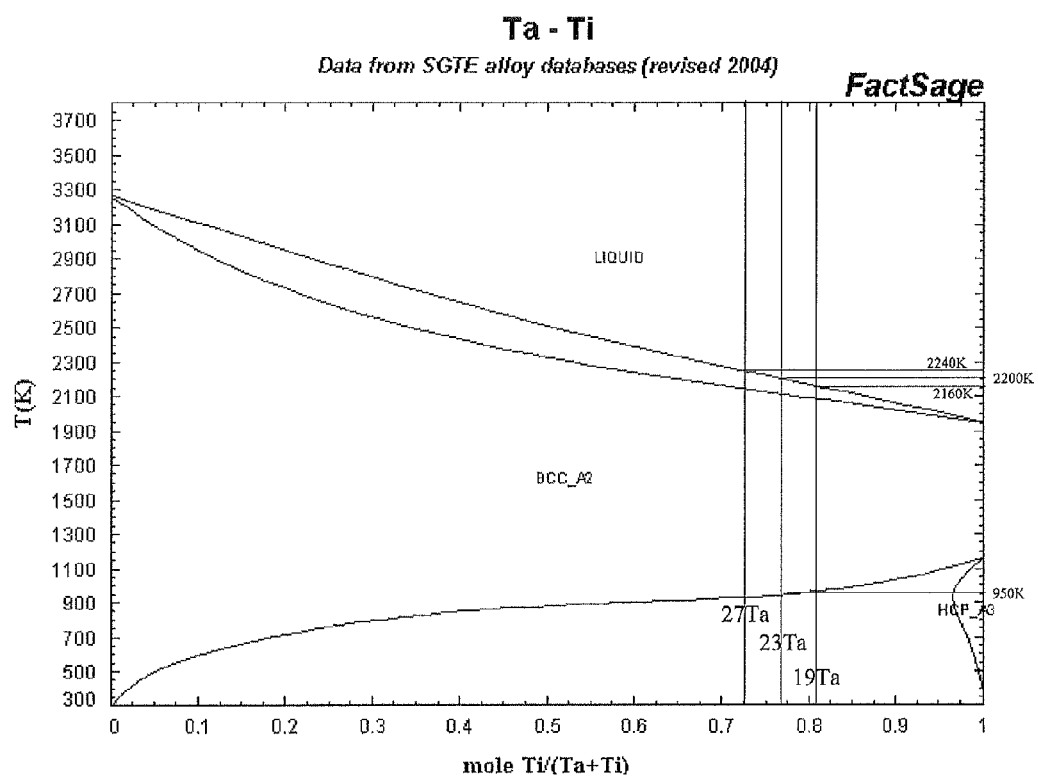
FIG. 1 is a Ti—Ta binary system phase diagram.

The upper limit of the content of Ta is set according to the melting point of the titanium alloy. FIG. 1 is a Ti—Ta binary system phase diagram. As shown in the figure, when the content of Ta exceeds 27%, the melting point of the titanium alloy can be about 2,000K or higher. In such a case, a special melting furnace is required, and therefore the production cost increases. In addition, a Ta raw material may not be completely melted. This may cause a reduction in the quality of the titanium alloy.

Even in view of the fact that the strength of the titanium alloy is likely to decrease when the content of Ta exceeds 27 at % and that the price of the Ta raw material is about 6 times higher than the price of a Ti raw material, the content of Ta is preferably 27 at % or less. Therefore, the content of Ta when the entire amount of the titanium alloy is taken as 100 at % is preferably 27 at % or less, more preferably 25 at % or less, and most preferably 24 at % or less.

The lower limit of the content of Ta is set according to the above-describe function of stabilizing the β phase and the mechanical properties of the titanium alloy as medical device materials, biocompatible materials, etc. More specifically, the function of stabilizing the β phase decreases as the content of Ta decreases. When the content of Ta is less than 15 at %, it is difficult to maintain the β phase at room temperature. Therefore, when the content of Ta is less than 15 at %, it is difficult to obtain the mechanical properties (Young's modulus, tensile strength, and elastic deformation strain) required for medical device materials, biocompatible materials, etc. even when tin (Sn) is added. Accordingly, the content of Ta when the entire amount of the titanium alloy is taken as 100 at % is preferably 15 at % or more, more preferably 19 at % or more, and most preferably 22 at % or more.

<Tin (Sn)>
Tin (Sn) has the function of suppressing precipitation of an ω phase that may cause an increase in Young's modulus and improving the superelastic effect of the titanium alloy.

The content of Sn when the entire amount of the titanium alloy is taken as 100 atomic % (at %) is preferably 0 to 8 at % and more preferably 1 to 6 at %.

Figure 2:
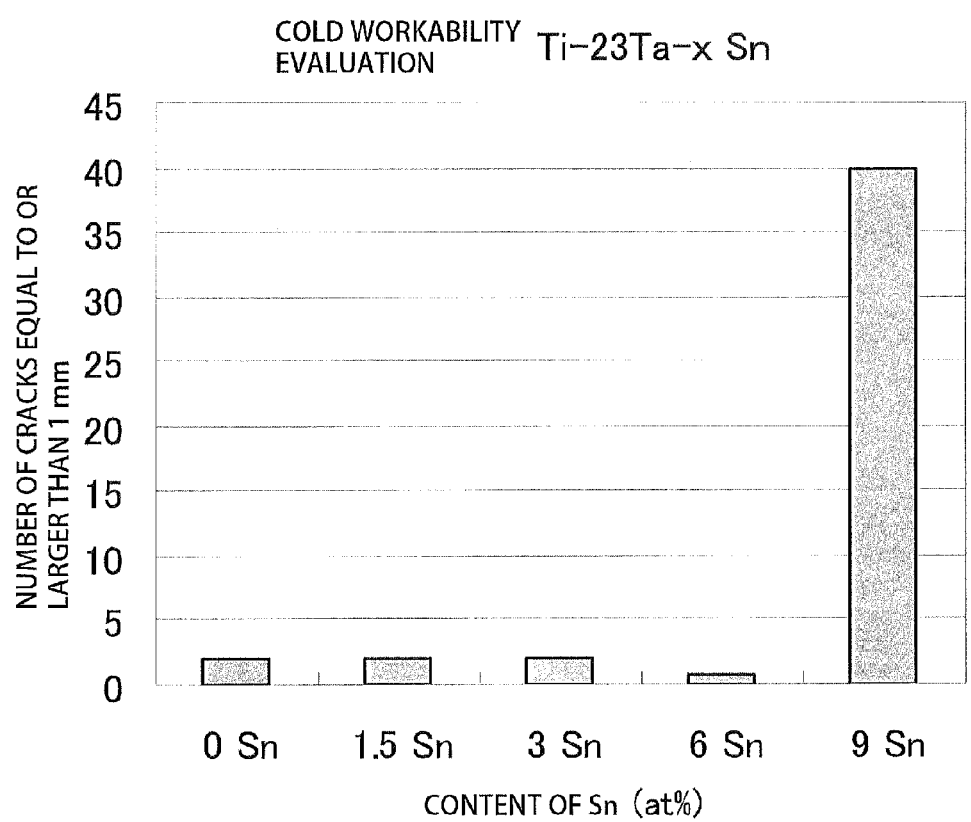
FIG. 2 is a graph showing the results of a cold workability evaluation test on titanium alloys (Ti-23Ta-xSn) containing Ta in an amount of 23 at %.

The upper limit of the content of Sn is set according to the workability (cold workability) of the titanium alloy. FIG. 2 is a graph showing the results of a cold workability evaluation test performed on titanium alloys (Ti-23Ta-xSn) containing Ta in an amount of 23 at % when the entire amount of each titanium alloy is taken as 100 atomic % (at %). Here, "x" is the content (at %) of Sn when the entire amount of the titanium alloy is taken as 100 at % and indicates that the content of Sn was changed. In this evaluation test, a plurality of test pieces (thickness: 1 mm, no heat treatment) having different contents x of Sn, i.e., 0 at %, 1.5 at %, 3 at %, 6 at %, and 9 at % when the entire amount of the titanium alloy is taken as 100 at %, were prepared. Each of the test pieces was cold-rolled (working rate: 86%) to a thickness of 0.1 mm, and the number of cracks with a length of 1 mm or longer in each of the cold-rolled test pieces was counted. The number of cracks was counted within the range of 140 mm in the rolling direction of each test piece.

As shown in FIG. 2, the results of the evaluation test show that the occurrence of cracks equal to or larger than 1 mm abruptly increases, i.e., the workability abruptly deteriorates, when the content of Sn is 9 at %. A similar trend was confirmed at different Ta contents. Therefore, the content of Sn when the entire amount of the titanium alloy is taken as 100 at % is preferably 8 at % or less and more preferably 6 at % or less, in order to obtain good workability.

No particular limitation is imposed on the lower limit of the content of Sn. More specifically, when the content of Ta is 15 at % or more, a titanium alloy having mechanical properties (Young's modulus, tensile strength, and elastic deformation strain) required for medical device materials, biocompatible materials, etc. can be obtained even though Sn is not added. However, to further improve the mechanical properties, it is preferable to add Sn. To sufficiently exert the above-described ω phase suppressing function, the content of Sn when the entire amount of the titanium alloy is taken as 100 at % is preferably 1 at % or more.

Although the details will be described later, the titanium alloy according to the present invention is an alloy in which the amounts of dissolution of metal ions of constituent elements, Ti, Ta, and Sn, are very small, which has high corrosion resistance, low cytotoxicity, and high biocompatibility, which is non-magnetic material unlikely to be magnetized by an external magnetic field and is very unlikely to adversely affect medical devices (such as MRI) that should be free from magnetism, and which has high elasticity, appropriate stiffness, and high workability. More specifically, the titanium alloy according to the present invention is a titanium alloy having lower cytotoxicity, higher magnetic properties, higher corrosion resistance, higher mechanical properties, and higher workability than those of the conventional titanium alloys. Therefore, the titanium alloy is suitable for medical tools such as medical guidewires, medical delivery wires, medical stents, medical clips, aneurysm embolization coils or vein filters, or dental cleansers, dental reamers, dental files or orthodontic wires, and is particularly preferable for forming a thin medical tool having a maximum outer diameter of about 0.005 mm to about 1 mm.

Of course, the titanium alloy according to the present invention is not limited to the above embodiment, and various modifications are possible without departing from the scope of the present invention. For example, any known method can be used to form, using the titanium alloy according to the present invention, medical guidewires, medical delivery wires, medical stents, medical clips, aneurysm embolization coils or vein filters, or dental cleansers, dental reamers, dental files or orthodontic wires, etc. Examples of such a method include wire drawing, drawing, casting, forging, and press working.

EXAMPLE 1

Examples of the titanium alloy according to the present invention will next be described in detail.
<Cytotoxicity Test>
1. Dissolution Test for Constituent Elements of Alloys Using Metal Powders (1) 25 mL of an RPMI-1640 (Roswell Park Memorial Institute) synthetic medium (hereinafter may be simply referred to as a "synthetic medium") sterilized in an autoclave was prepared in a polypropylene-made centrifuge tube. Then 2 g of a metal powder was immersed in the synthetic medium, and dissolution was performed in a shaking thermostatic bath at 37° C. for 10 days. Eight types of metal materials, i.e., Fe, Ni, Cr, Co, Ti, Ta, Sn, and Al, were prepared.

(2) Each solution in (1) was filtrated through a filter having a pore size of 0.2 μm to remove the metal powder in the synthetic medium.

(3) 1 mL of the synthetic medium in (2) was collected into a test tube and subjected to pyrolysis with concentrated nitric acid, and the concentration of dissolved metal ions was measured by ICP analysis.

2. Anodic Polarization Test (4) 500 mL of phosphate buffered saline (PBS) was used as a simulated body fluid.

(5) An anodic polarization test was performed using a potentiostat (manufactured by Solartron) on metal wires, i.e., TiTaSn wires (Ta: 15, 19, and 23 at %, Sn: 0, 3, and 6 at %, Ti+unavoidable impurities: balance), a SUS316 wire (JIS standard G4305), a CoCrMo wire (Cr: 29 at %, Mo: 6 at %, Co+unavoidable impurities: balance), and a TiNi wire (Ti: 49.5 at %, Ni+unavoidable impurities: balance).

(6) Each wire was used as a working electrode, a Pt wire was used as a counter electrode, and Hg/HgCl was used as a reference electrode.

(7) Voltage of −1 V to +2 V (vs SCE) was applied to the working electrode at a sweep rate of 0.33 mV/sec, and the current (current density) flowing to the counter electrode was measured.

3. Cytotoxicity Test Using Metal Corrosion Solutions (8) Mouse fibroblast cells L929 and human thymus-derived macrophage precursor cells U937 were used for the cytotoxicity test.

(9) L-glutamine, 7 wt % sodium bicarbonate, and 10 vol % FBS (Fetal Bovine Serum) were added to an Eagle's MEM synthetic medium to prepare a culture solution for the L929. These were added to an RPMI-1640 synthetic medium to prepare a culture solution for the U937.

(10) The U937 was used for the test after differentiation to macrophages. Therefore, 0.32 μL/mL of PMA (Phorbol 12-Myristate 13-Acetate) had been added to the culture solution in the above (9) for differentiation.

(11) A wire of TiTaSn (Ta: 23 at %, Sn: 3 at %, Ti+unavoidable impurities: balance) was subjected to anodic electrodissolution in 100 mL of a synthetic medium using a potentiostat to prepare a corrosion solution. Then corroded-metal concentration-controlled culture solutions (hereinafter referred to as test solutions) of 64 ppm, 32 ppm, 16 ppm, 8 ppm, 4 ppm, 2 ppm, 1 ppm, and 0 ppm were prepared.

(12) The same procedure as in (11) was repeated using SUS316, CoCrMo, and TiNi as controls to produce test solutions.

(13) The human thymus-derived U937 macrophage precursor cells were mixed with the culture solution in (10) at a cell density of $1\times10^5$ Cells/mL, and 200 µL of the mixture was added to a 96-well microplate and cultured in a 37° C. incubator at 5% $CO_2$ and a humidity of 100% for 24 hours to differentiate the U937 to macrophages.

(14) The culture solution was replaced with the test solutions, and the culture was further continued in the incubator in (13) for 24 hours.

(15) The microplate was centrifuged at 1,800 rpm for 10 minutes, and 100 µL of the supernatant of each of the culture solutions in the wells was collected.

(16) The concentration of lactate dehydrogenase released into each well in (15) was measured using an LDH CDK (Cytotoxicity Detection Kit) (manufactured by Takara Bio Inc.), and the content of LDH was quantified using an ELISA plate reader.

Figure 3:
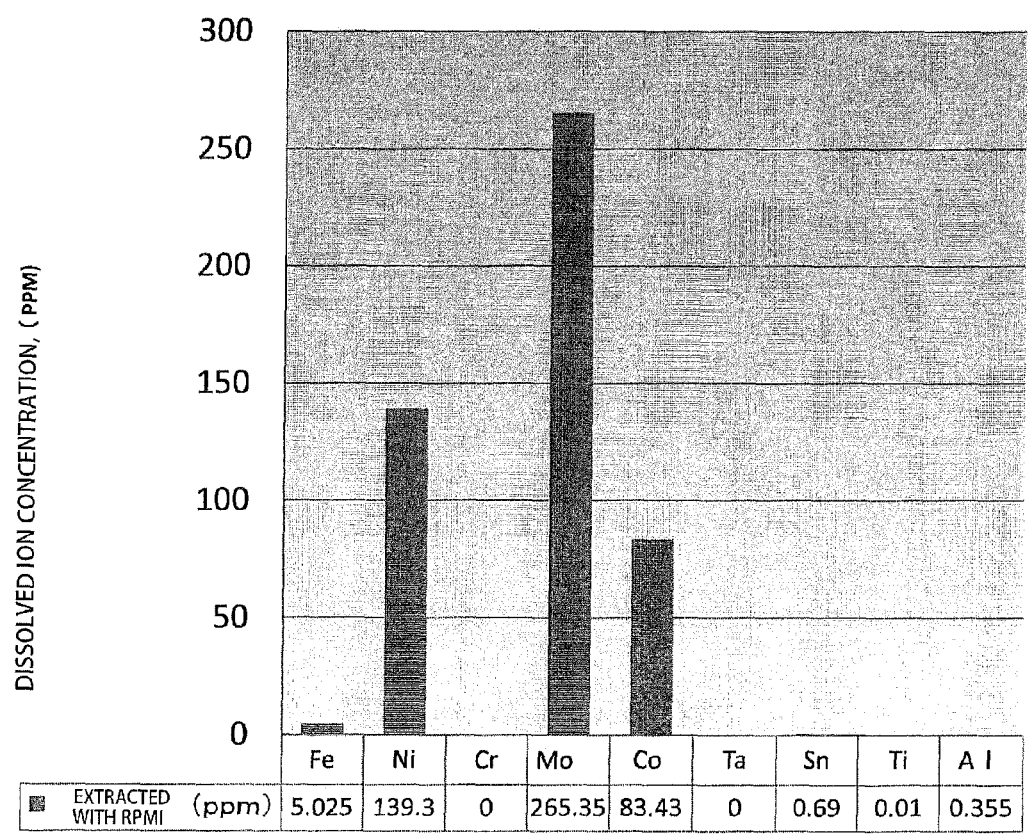
FIG. 3 is a graph showing the dissolution amounts of ions dissolved from metal powders in a synthetic medium.
Figure 4:
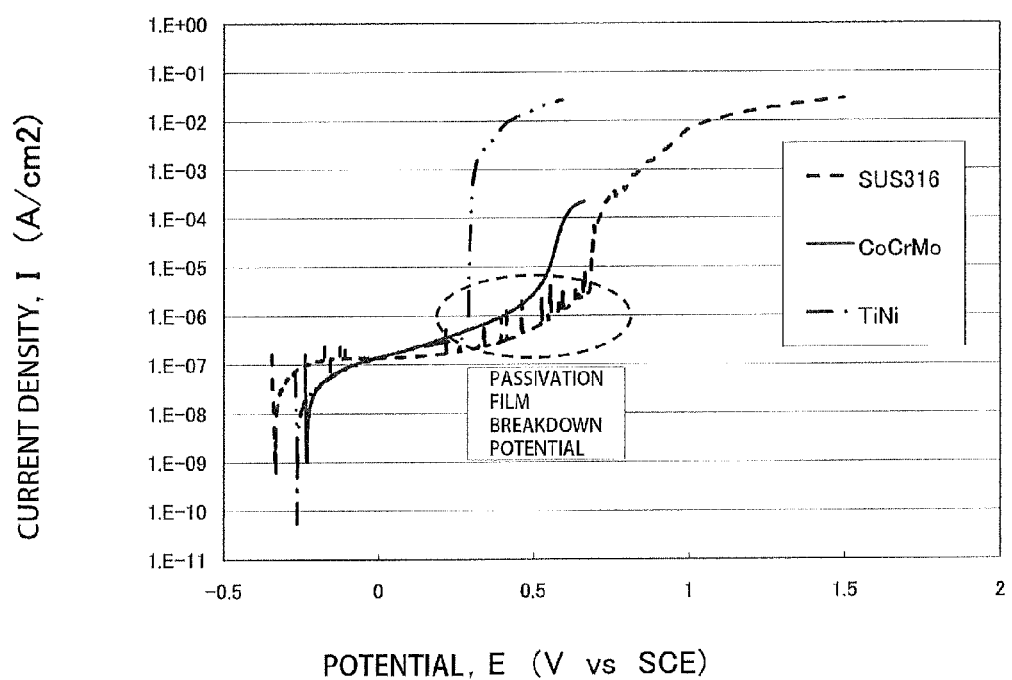
FIG. 4 is a graph showing the results of an anodic polarization test on metal wires (SUS316, CoCrMo, and TiNi).
Figure 5:
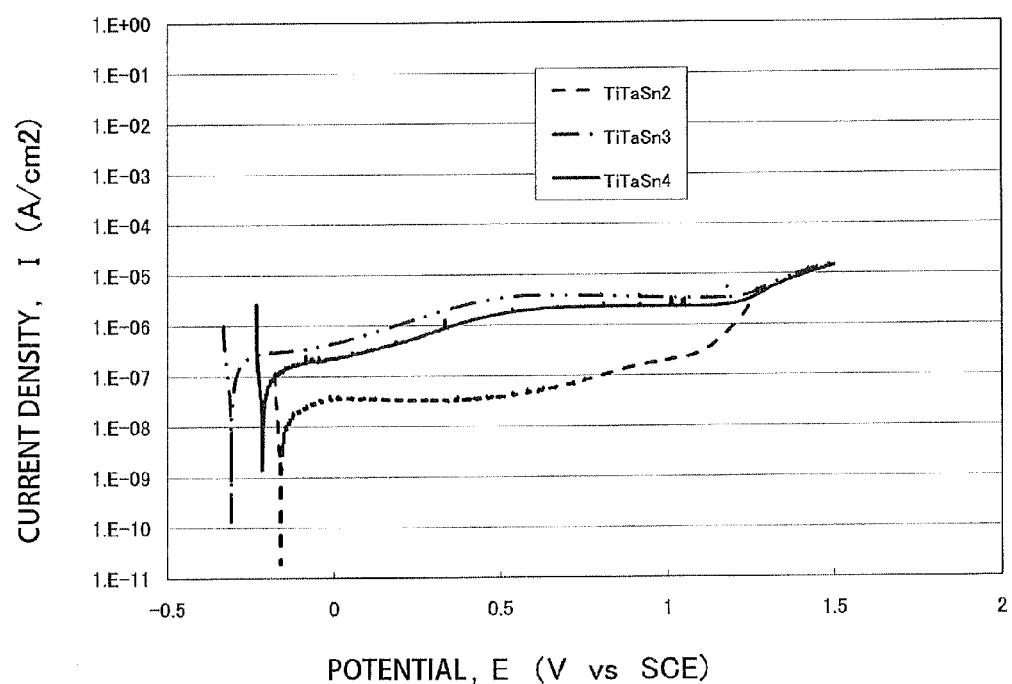
FIG. 5 is a graph showing the results of the anodic polarization test on metal wires (TiTaSn).
Figure 6:
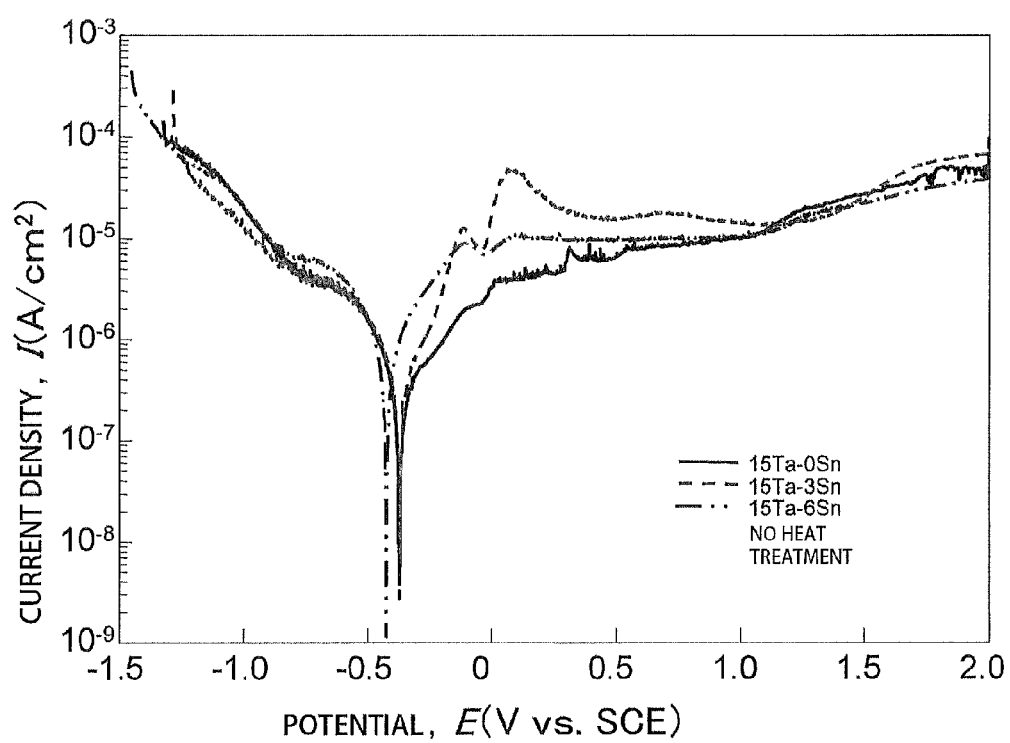
FIG. 6 is a graph showing the results of the anodic polarization test on metal wires (TiTaSn).
Figure 7:
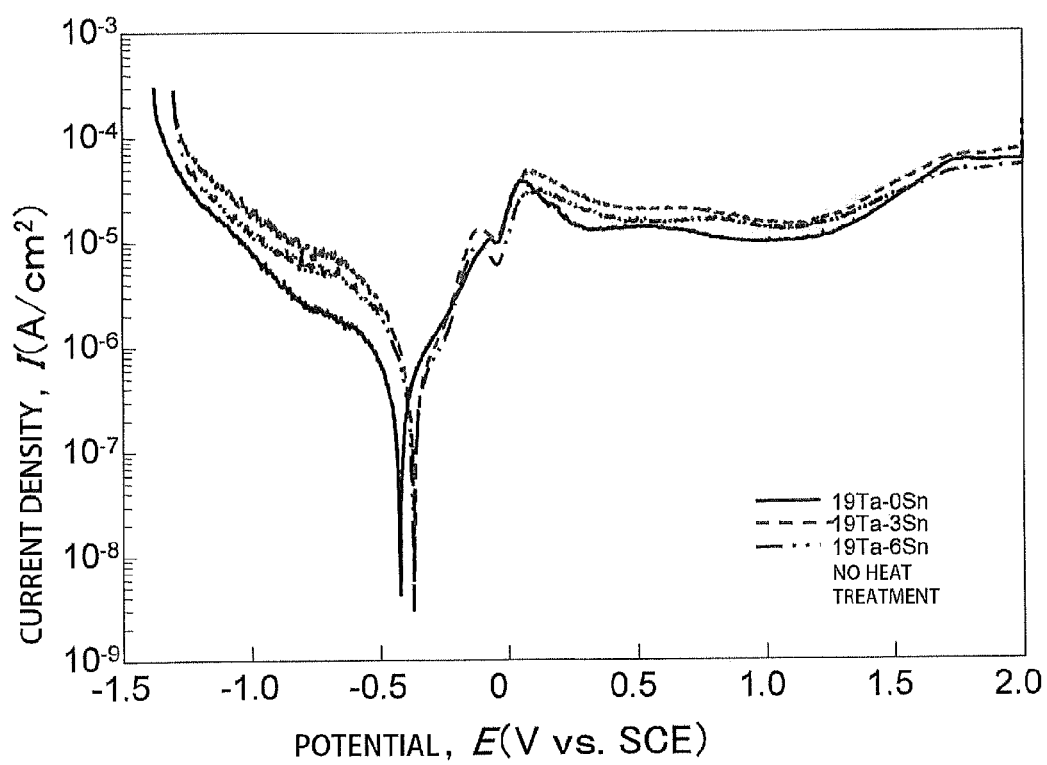
FIG. 7 is a graph showing the results of the anodic polarization test on metal wires (TiTaSn).
Figure 8:
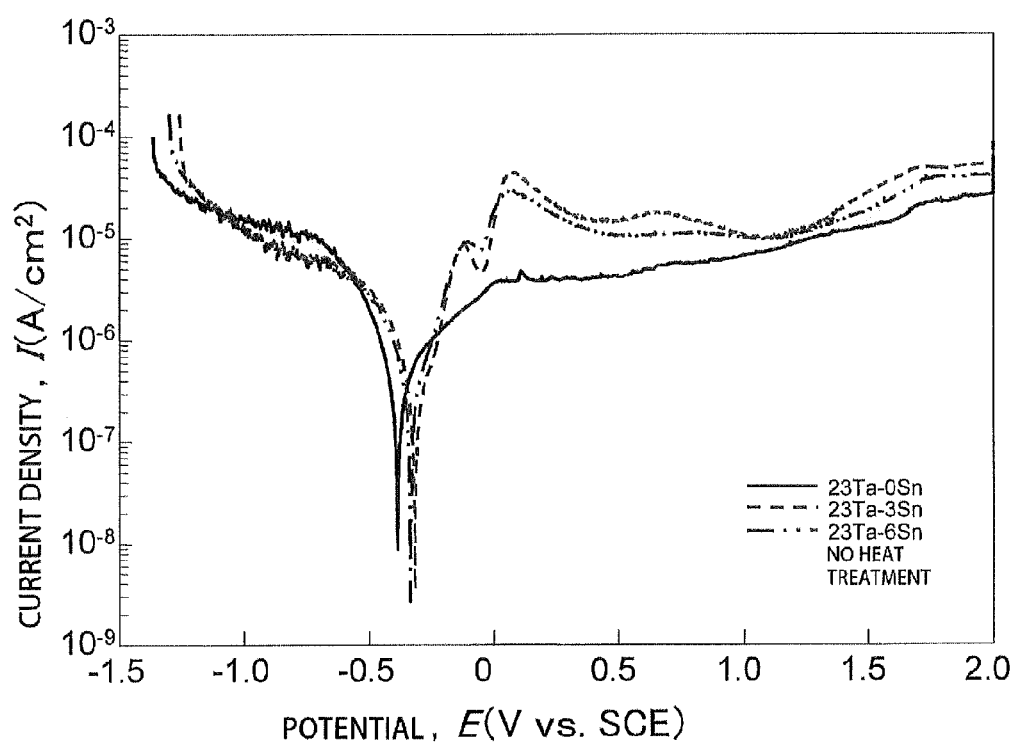
FIG. 8 is a graph showing the results of the anodic polarization test on metal wires (TiTaSn).
Figure 9:
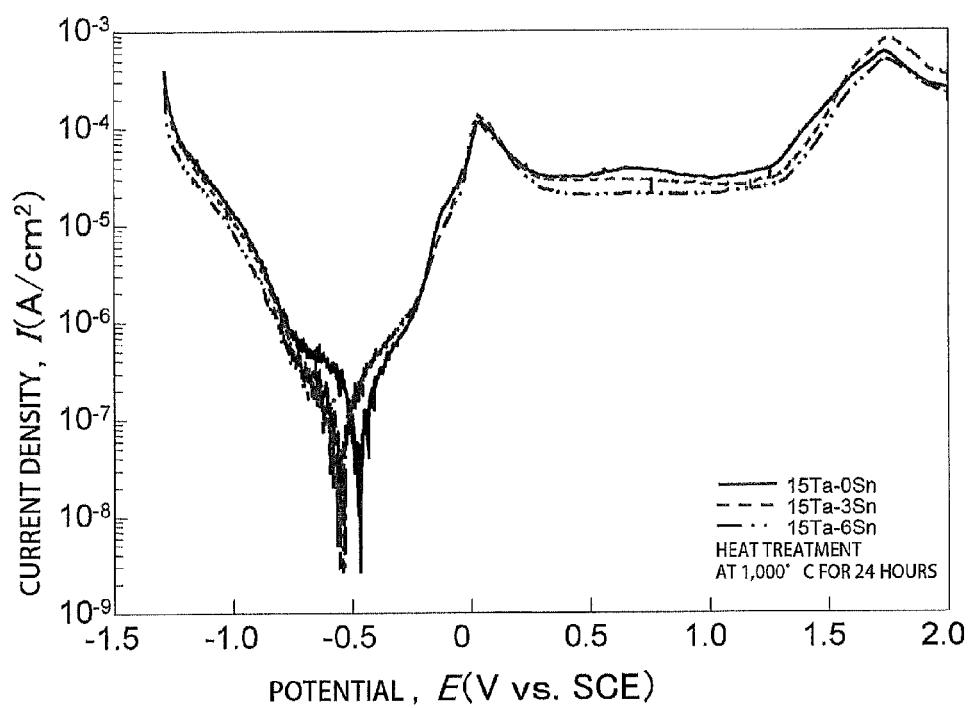
FIG. 9 is a graph showing the results of the anodic polarization test on metal wires (TiTaSn).
Figure 10:
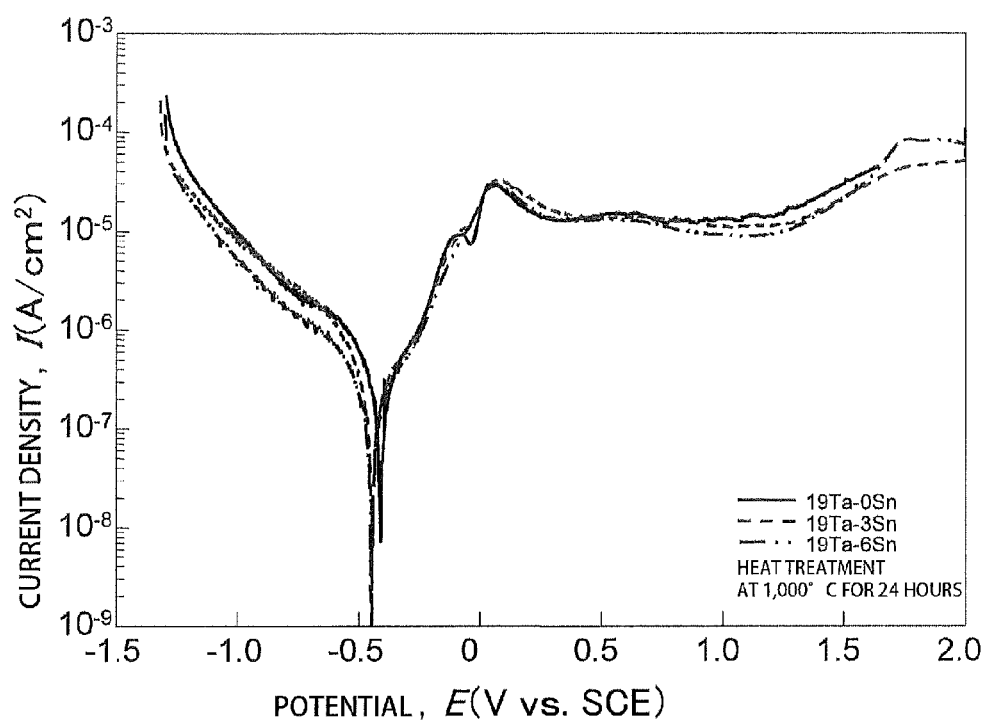
FIG. 10 is a graph showing the results of the anodic polarization test on metal wires (TiTaSn).
Figure 11:
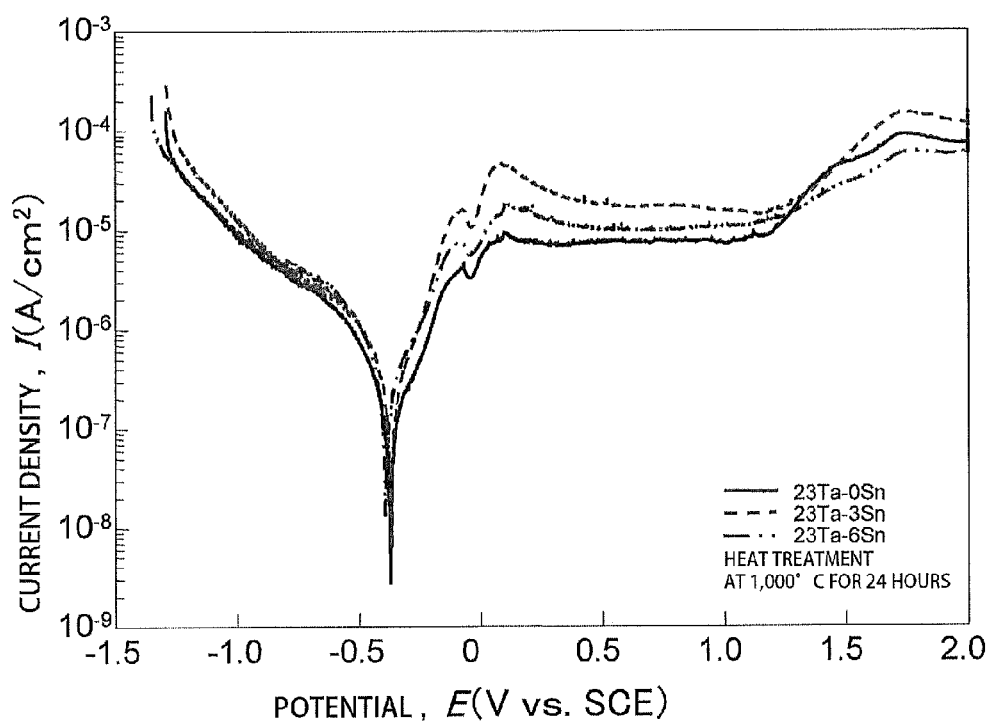
FIG. 11 is a graph showing the results of the anodic polarization test on metal wires (TiTaSn).

FIG. 3 shows the dissolution amounts of ions dissolved from the metal powders in the synthetic medium, and FIGS. 4 to 11 shows the results of the anodic polarization test on the metal wires. FIG. 5 shows the results of the anodic polarization test on TiTaSn (Ta: 23 at %, Sn: 3 at %, Ti+unavoidable impurities: balance) samples. In FIG. 5, TiTaSn2 represents a sample heat-treated at a temperature of 450° C., TiTaSn3 represents a sample heat-treated at a temperature of 650° C., and TiTaSn4 represents a sample heat-treated at a temperature of 750° C. FIGS. 6 to 11 show the results of the anodic polarization test on TiTaSn samples (Ta: 15, 19, and 23 at %, Sn: 0, 3, and 6 at %, Ti+unavoidable impurities: balance). FIGS. 6 to 8 show the results of test on samples with no heat treatment, and FIGS. 9 to 11 show the results of the test on samples subjected to heat treatment at 1,000° C. for 24 hours. 15Ta-0Sn, for example, in FIGS. 6 to 11 represents TiTaSn (Ta: 15 at %, Sn: 0 at %, Ti+unavoidable impurities: balance), and 19Ta-3Sn, for example, represents TiTaSn (Ta: 19 at %, Sn: 3 at %, Ti+unavoidable impurities: balance).

As can be seen from the results of the dissolution test shown in FIG. 3, it was confirmed that the amounts of dissolution of metal ions of the constituent elements, Ti, Ta, and Sn, in the synthetic medium used as the simulated body fluid were much smaller than the amounts of dissolution of metal ions of the constituent elements of SUS316, TiNi, and CoCrMo. As can be seen from the results of the anodic polarization test shown in FIGS. 4 to 11, it was confirmed that the corrosion resistance of TiTaSn was higher than that of existing medical biomaterials. More specifically, it was confirmed that TiTaSn (Ta: 15, 19, or 23 at %, Sn: 0, 3, or 6 at %, Ti+unavoidable impurities: balance) had features in that an abrupt increase in current density at 1 V or lower that occurs in SUS316, TiNi, and CoCrMo did not occur, that a gradual increase in current density was maintained until at least about 2 V, that a passivation region was wider than those of the above materials, and that pitting corrosion was less likely to occur.

Figure 12:
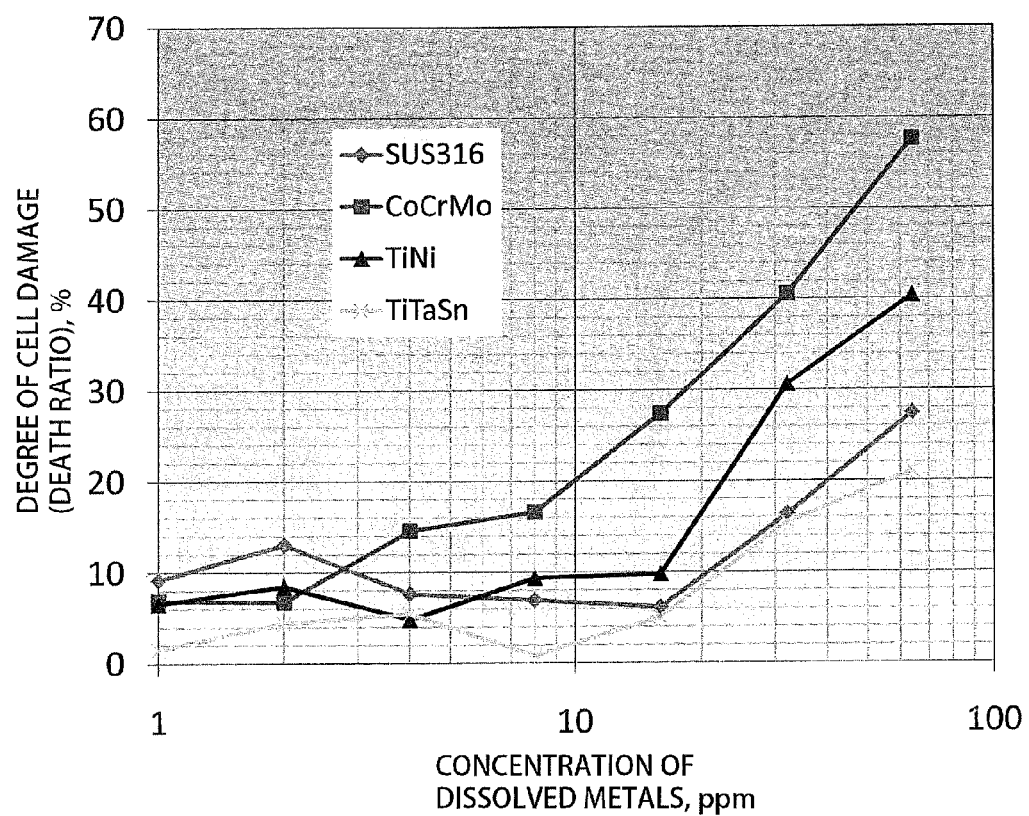
FIG. 12 is a graph showing the relationship between the degree of cell damage and the concentration of dissolved metals obtained in a cytotoxic test on L929 cells.
Figure 13:
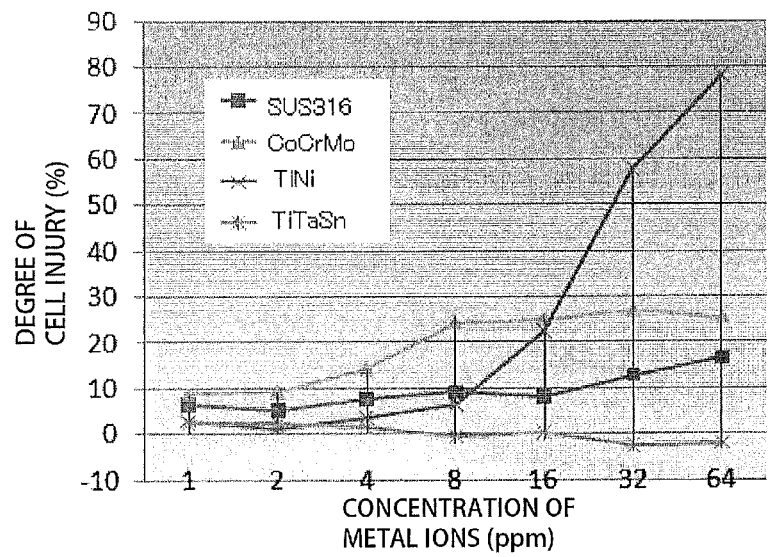
FIG. 13 is a graph showing the relationship between the degree of cell injury and the concentration of metal ions obtained in the cytotoxic test on U937 macrophages.

FIGS. 12 and 13 show the relationship between the degree of cell injury (the degree of cell damage) and the concentration of a metal corrosion solution for the L929 cells and U937 macrophages in the metal corrosion solution. The concentrations of metal ions (concentrations of dissolved metals) in the metal corrosion solutions were values measured by ICP emission spectrometry. The degree of cell injury is one index that indicates the strength of cytotoxicity and is defined by the following formula.

Degree of cell injury (%)=(experimental value– low control)/(high control–low control)×100

Here, the high control is the concentration of LDH released into the culture solution when all the cells are broken with Triton-X, and the low control is the concentration of LDH released from untreated cells. The experimental value is the concentration of LDH released from cells when corroded metals are added at a predetermined concentration.

As can be seen from the results of the cytotoxicity test shown in FIG. 12, it was confirmed that the degree of cell injury for the L929 cells by the TiTaSn example sample (Ta: 23 at %, Sn: 3 at %, Ti+unavoidable impurities: balance) tended to be generally lower than those by SUS316, TiNi, and CoCrMo. More specifically, the degree of cell injury for the L929 cells by the TiTaSn example sample was confirmed to be less than 10% when the metal ion concentration measured by ICP emission spectrometry was 16 ppm or less, to be less than 20% when the metal ion concentration was 32 ppm or less, and to be less than 22% when the metal ion concentration was 64 ppm or less. The rate of increase in the degree of cell injury for the L929 cells by the TiTaSn example sample tended to be high (i.e., the gradient in the graph tended to increase) when the metal ion concentration was 16 ppm or higher. However, the rate of increase was smaller than those by SUS316, TiNi, and CoCrMo. More specifically, it was confirmed that the TiTaSn example sample has lower toxicity (lower cytotoxicity) than SUS316, TiNi, and CoCrMo even at a metal concentration of 64 ppm or higher, which is a very high concentration for a living body, and therefore has higher biocompatibility.

The rate of increase in the degree of cell injury for the L929 cells by SUS316 was $(27-6)/(64-16)\cong0.44$ when the metal ion concentration was 16 ppm to 64 ppm, and the rate of increase in the degree of cell injury for the L929 cells by TiNi was $(40-10)/(64-16)\cong0.63$ when the metal ion concentration was 16 ppm to 64 ppm. The rate of increase in the degree of cell injury for the L929 cells by CoCrMo was $(57.5\times27.5)/(64-16)\cong0.63$ when the metal ion concentration was 16 ppm to 64 ppm. However, the rate of increase in the degree of cell injury for the L929 cells by the TiTaSn example sample was $(21-5)/(64-16)\cong0.33$ when the metal ion concentration was 16 ppm to 64 ppm. More specifically, the rate of increase in the degree of cell injury for the L929 cells by the TiTaSn example sample was confirmed to be smaller than the rate of increase for SUS316, i.e., 0.44, when the metal ion concentration was 16 ppm or higher.

As can be seen from the results of the cytotoxicity test shown in FIG. 13, it was confirmed that the degree of cell injury for the U937 macrophages by the TiTaSn example sample (Ta: 23 at %, Sn: 3 at %, Ti+unavoidable impurities: balance) tended to be generally lower than those by SUS316, TiNi, and CoCrMo. More specifically, the degree of cell injury for the U937 macrophages by the TiTaSn example sample varied within the range of about ±2% when the metal ion concentration was 1 ppm to 64 ppm, and no tendency of increase was confirmed. Therefore, as can also be seen from these test results, it was confirmed that the TiTaSn example sample has lower toxicity than SUS316, TiNi, and CoCrMo even at a metal concentration of 64 ppm or higher, which is a very high concentration for a living body, and therefore has higher biocompatibility.

Incidentally, the degree of cell injury for the U937 macrophages by SUS316 tended to increase when the metal ion concentration was 16 ppm or higher and became 10% or higher when the metal ion concentration was 32 ppm or higher. The degree of cell injury for the U937 macrophages by TiNi tended to increase when the metal ion concentration was 8 ppm or higher and became 20% or higher when the metal ion concentration was 16 ppm or higher. The degree of cell injury for the U937 macrophages by CoCrMo tended to increase when the metal ion concentration was 2 ppm or higher and became 10% or higher when the metal ion concentration was 4 ppm or higher. However, the degree of cell injury for the U937 macrophages by the TiTaSn example sample was less than 2% over the entire range in which the metal ion concentration was 64 ppm or lower. More specifically, it was confirmed that the degree of cell injury for the U937 macrophages by the TiTaSn example sample can be sufficiently maintained to less than 10% when the metal ion concentration measured by ICP emission spectrometry is 64 ppm or less and that the TiTaSn example sample has lower toxicity than SUS316 having relatively low toxicity but causing the degree of cell injury for the U937 macrophages to be 10% or higher when the metal ion concentration is 32 ppm or higher and therefore has higher biocompatibility.

<Magnetic Characteristics Test>

A magnetic characteristics test was performed in order to evaluate the magnetic characteristics of the titanium alloy according to the present invention. In the magnetic characteristics test, an alloy material of TiTaSn (Ta: 23 at %, Sn: 3 at %, Ti+unavoidable impurities: balance) was used as an example sample, and an alloy material of TiNi (Ni: 54.94 at %, Ti+unavoidable impurities: balance) was used as a comparative example sample. Each of the example sample and comparative example sample used was a circular rod sample having a diameter φ of 0.5 mm and a length of 7 mm, and each sample was secured to a vibrating rod of a VSM (Vibrating Sample Magnetometer) to measure the magnetic characteristics.

Figure 14:
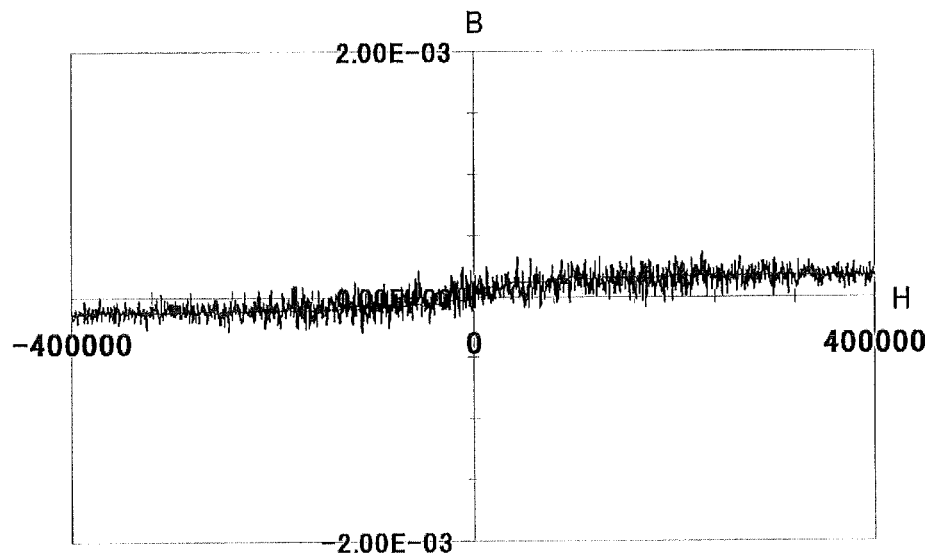
FIG. 14 is a graph showing a B-H curve of a TiTaSn example sample.
Figure 15:
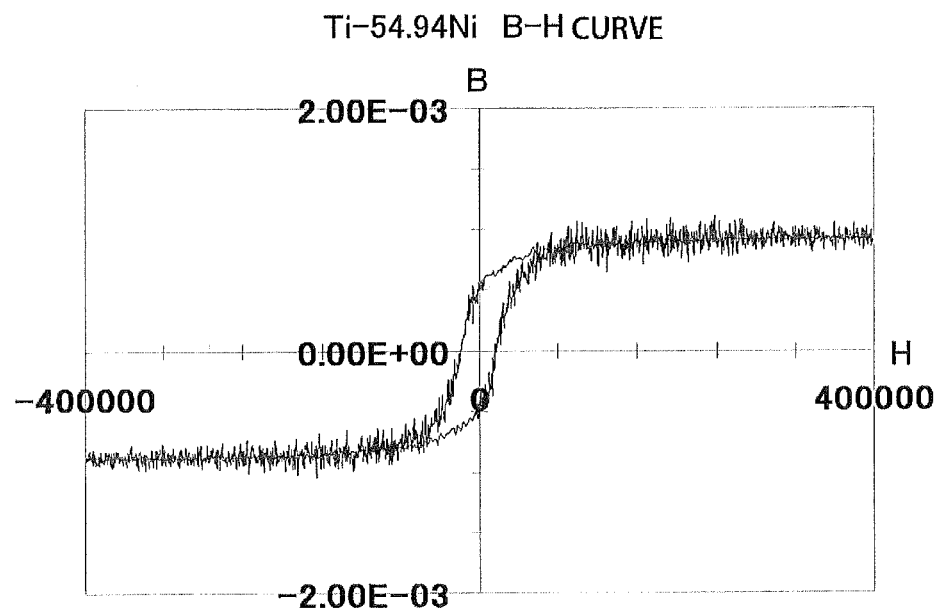
FIG. 15 is a graph showing a B-H curve of a TiNi comparative example sample.

FIG. 14 shows the B-H curve of the TiTaSn example sample, and FIG. 15 shows the B-H curve of the TiNi comparative example sample. The vertical axis B in each figure represents a magnetic flux density (T: tesla), and the horizontal axis H represents the intensity of a magnetic field (A/m). As can be seen from the results of the magnetic characteristics test, the saturation magnetic flux density of the TiTaSn example sample was $5.0 \times 10^{-4}$ T (tesla) or lower when the intensity of an external magnetic field was $4.0 \times 10^{5}$ A/m. Therefore, the TiTaSn example sample was confirmed to be a non-magnetic material that is less likely to be magnetized by the external magnetic field than the TiNi comparative example sample alloy having a saturation magnetic flux density of higher than $1.0 \times 10^{-3}$ T (tesla).

A large number of medical devices such as MRI using magnetism are present in medical sites, and, in some cases, an examination is performed on a patient in a strong magnetic field environment. However, the TiTaSn alloy according to the present invention is a non-magnetic material unlikely to be magnetized by the external magnetic field and is therefore very unlikely to adversely affect the medical devices that should be free from magnetism. Therefore, the TiTaSn alloy is a material particularly suitable for medical guidewires, medical delivery wires, medical stents, medical clips, aneurysm embolization coils or vein filters, or dental cleansers, dental reamers, dental files or orthodontic wires that are used in medical sites.

<Three-Point Bending Test>

Figure 16:
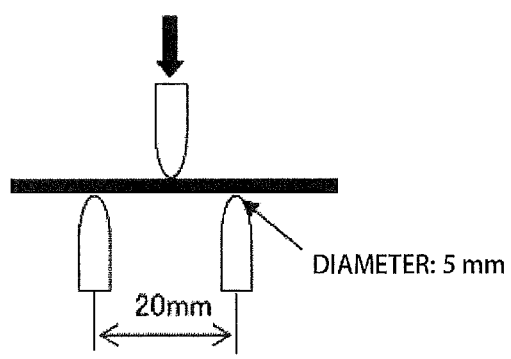
FIG. 16 is a diagram schematically illustrating the method of a three-point bending test.

To evaluate the mechanical properties of the titanium alloy according to the present invention, a three-point bending test was performed. In the three-point bending test, an alloy material of TiTaSn (Ta: 23 at %, Sn: 3 at %, Ti+unavoidable impurities: balance) was used as an example sample, and an alloy material of TiNi (Ni: 54.94 at %, Ti+unavoidable impurities: balance) was used as a comparative example sample. Each of the example sample and comparative example sample used was a circular rod sample having a diameter φ of 0.5 mm, and the three-point bending test was performed on these samples by the method shown in FIG. 16 to measure the amount of recovery. The measurement conditions are as follows. The distance between two supporting members was 20 mm, the diameter of the pointed end of each of the two supporting members and one pressing member was 5 mm (pointed end R: 2.5 mm), and the rate of pressing was 1 mm/minute.

The method of the three-point bending test is as follows.

(1) First, the pressing member was pressed 0.5 mm toward a sample from an initial position (the position at which the pointed end of the pressing member was in contact with the sample) and then returned until the load became 0. Then the amount of deformation (mm) at this point was measured.

(2) Next, the pressing member was pressed 1 mm toward the sample from the initial position, and the load was released. Then the amount of deformation of the sample was measured.

(3) Then the pressing depth of the pressing member was increased by 0.5 mm, and the amount of deformation of the sample was measured. The measurement was repeated until the pressing depth reached 4 mm.

(4) Finally, the amount of recovery (%) relative to the pressing depth was computed using the amounts of deformation measured in (1) to (3) above.

Figures 17, 18:
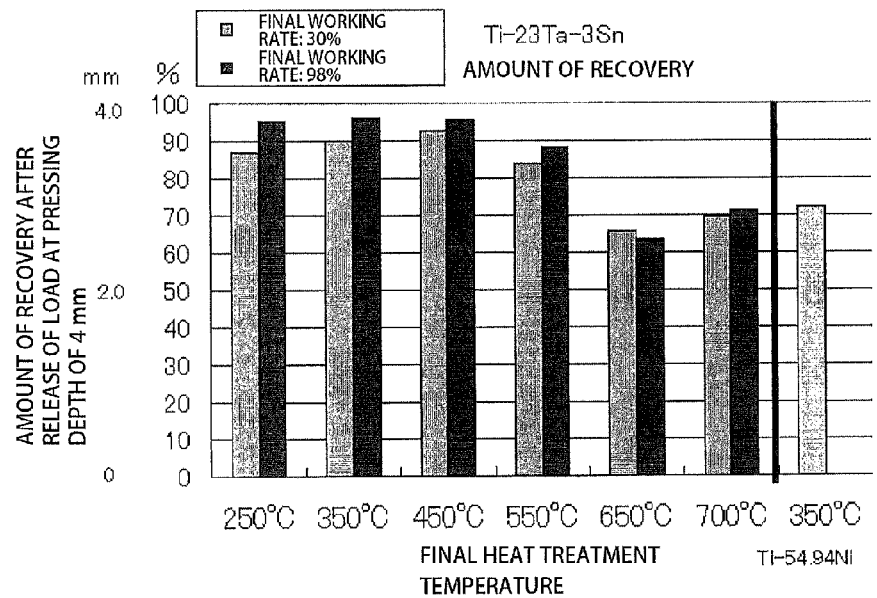
FIG. 17 is a graph showing the amounts of recovery of TiTaSn example samples (final heat treatment temperatures: 250° C., 350° C., 450° C., 550° C., 650° C., and 700° C.)
FIG. 18 is a table showing the types of example samples subjected to a tensile test.

FIG. 17 shows the amounts of recovery of the TiTaSn example samples (final heat treatment temperatures: 250° C., 350° C., 450° C., 550° C., 650° C., and 700° C.) and the amount of recovery of the TiNi comparative example sample (final heat treatment temperature: 350° C.). Among two bars for each final heat treatment temperature in FIG. 17, the left bar represents a sample with a final working rate of 30%, and the right bar represents a sample with a final working rate of 98% (the same applies to FIGS. 19 and 20). As can be seen from the results of the three-point bending test shown in the figure, the amount of recovery of each TiTaSn example sample after the pressing member was pressed to a pressing depth of 4 mm at a pressing rate of 1 mm/minute and then the load was released was confirmed to be 60% or higher. It was also confirmed that the amount of recovery (about 90%) of the TiTaSn example sample with a final heat treatment temperature of 350° C. and a final working rate of 30% was larger than the amount of recovery (about 70%) of the TiNi comparative example sample with a final heat treatment temperature of 350° C. and a final working rate of 30%.

<Tensile Test>

A tensile test was performed in order to evaluate the mechanical properties of the titanium alloy according to the present invention. FIG. 18 is a table showing the types of example samples subjected to the tensile test. As shown in the figure, in the tensile test, seven types of TiTaSn alloy materials of sample Nos. T1 to T7 with different contents (at %) of Ta and Sn were used as the example samples. The example samples used were circular wire samples having a diameter φ of 0.5 mm, and the tensile test was performed on these samples using a tensile tester. The measurement conditions are as follows: the gauge length: 50 mm, the tensile rate: 1 mm/minute. To determine the Young's modulus, a stress-strain curve was measured during the tensile test in the tensile tester according to JIS H 7103 (2002), and the Young's modulus was determined from the gradient of a stress increase line at stresses equal to or lower than a yield point. Stress-strain was repeatedly applied to each example sample to rupture the example sample, and the elongation of the example sample with a residual strain of 0.5% (elastic deformation strain, elastic limit) was measured.

Figure 19:
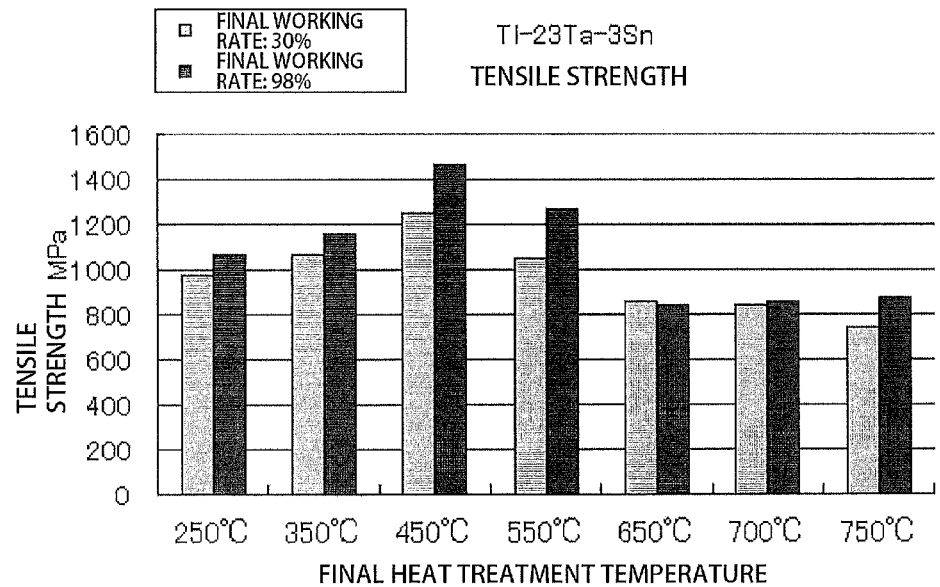
FIG. 19 is a graph showing the tensile strengths of TiTaSn example samples of sample No. T3 (final heat treatment temperatures: 250° C., 350° C., 450° C., 550° C., 650° C., 700° C., and 750° C.).

FIG. 19 shows the tensile strengths of TiTaSn example samples of sample No. T3 (final heat treatment temperatures: 250° C., 350° C., 450° C., 550° C., 650° C., 700° C., and 750° C.). As can be seen from the results of the tensile test, it was confirmed that the tensile strengths of the TiTaSn example samples of sample No. T3 were within the range of 600 MPa to 1,600 MPa.

Figure 20:
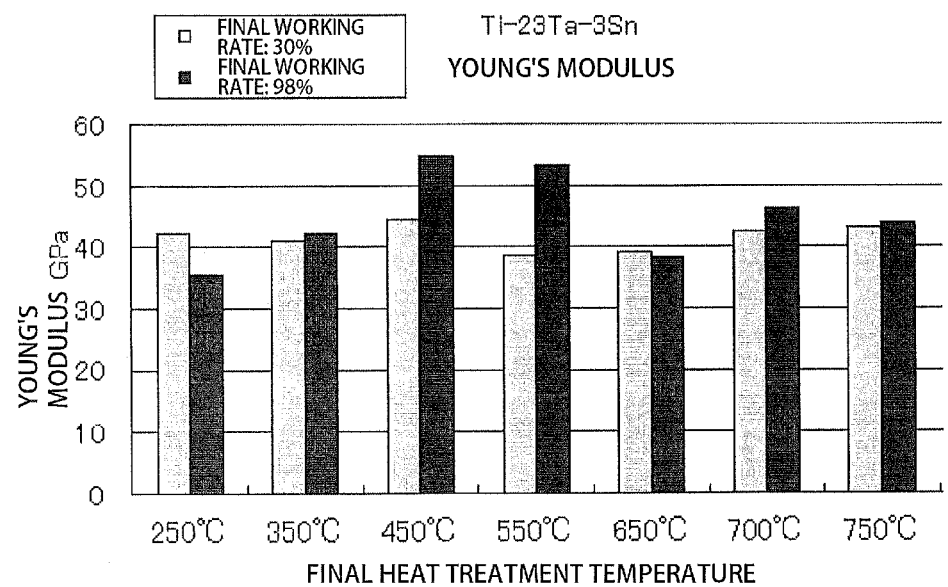
FIG. 20 is a graph showing the Young's moduli of TiTaSn example samples of sample No. T3 (final heat treatment temperatures: 250° C., 350° C., 450° C., 550° C., 650° C., 700° C., and 750° C.)

FIG. 20 shows the Young's moduli of the TiTaSn example samples of sample No. T3 (final heat treatment temperatures: 250° C., 350° C., 450° C., 550° C., 650° C., 700° C., and 750° C.). As can be seen from the results of the tensile test, it was confirmed that the Young's moduli of the TiTaSn example samples of sample No. T3 were within the range of 30 GPa to 85 GPa.

Figure 21:
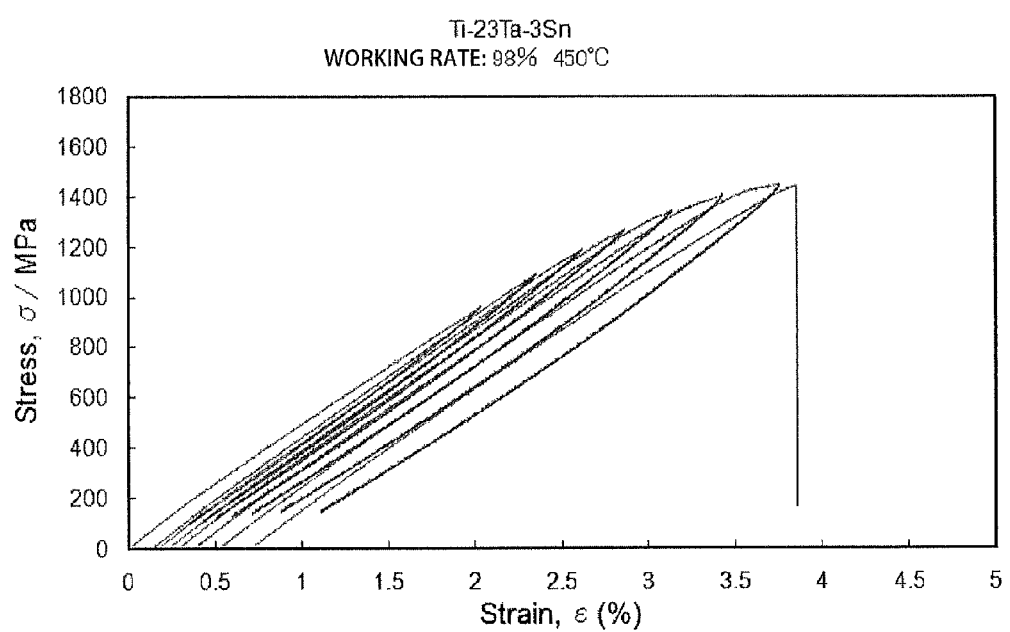
FIG. 21 is a graph showing the results of the tensile test performed on a TiTaSn example sample of sample No. T3 (final working rate: 98%, final heat treatment temperature: 450° C.), the tensile test being performed by repeatedly applying stress-strain until the sample ruptures.

FIG. 21 shows the results of the tensile test in which stress-strain was repeatedly applied to a TiTaSn example sample of sample No. T3 (final working rate: 98%, final heat treatment temperature: 450° C.) to rupture the sample. As can be seen from the results of the tensile test, it was confirmed that the elongation with a residual strain of 0.5% was about 3.4 to about 3.7%. Similar tensile tests were performed, and the results were confirmed as follows. The elongation of a TiTaSn example sample of sample No. T3 (final working rate 98%, no final heat treatment) with a residual strain of 0.5% was about 3.2 to about 3.6%. The elongation of a TiTaSn example sample of sample No. T3 (final working rate: 98%, final heat treatment temperature: 250° C.) with a residual strain of 0.5% was about 3.4 to about 3.6%. The elongation of a TiTaSn example sample of sample No. T3 (final working rate: 98%, final heat treatment temperature: 650° C.) with a residual strain of 0.5% was about 2.1 to about 2.6%.

Figure 23:
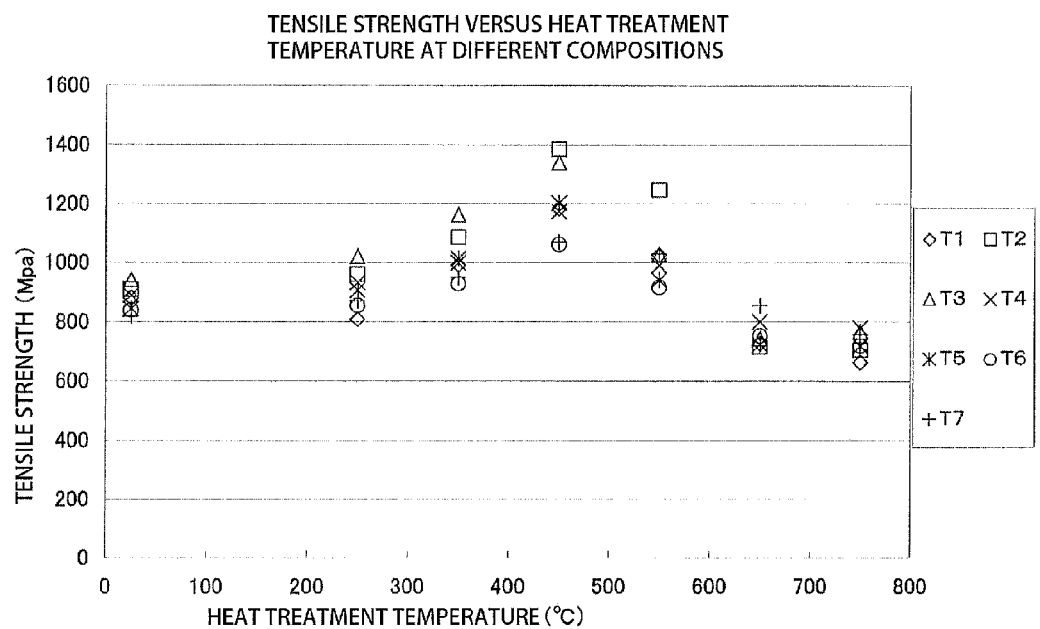
FIG. 23 is a graph showing the tensile strengths of the TiTaSn example samples of sample Nos. T1 to T7 (final heat treatment temperatures: 25° C., 250° C., 350° C., 450° C., 550° C., 650° C., and 750° C.)
Figure 24:
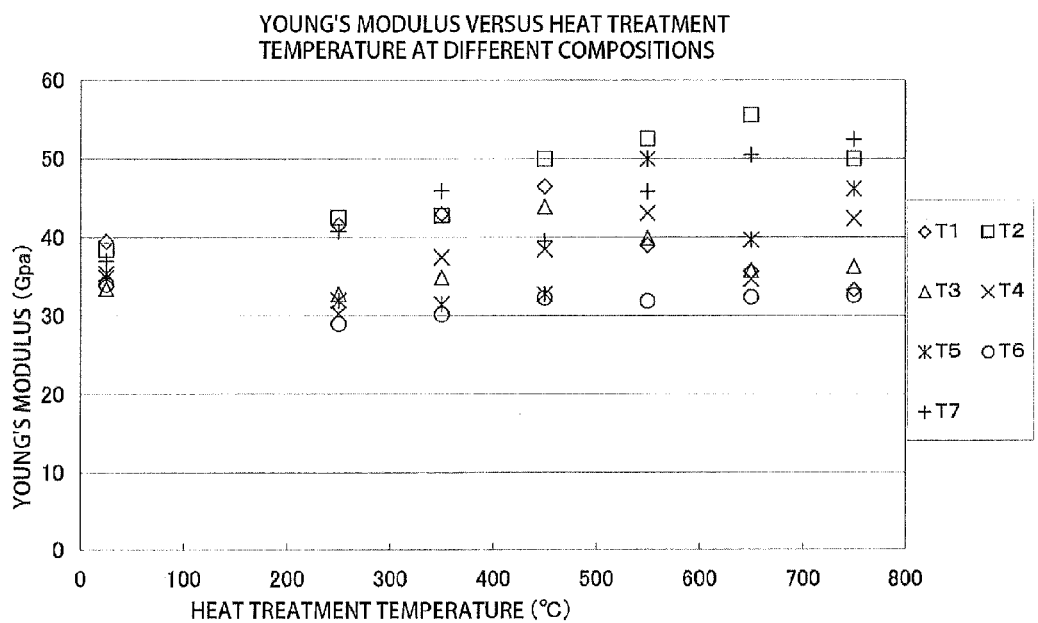
FIG. 24 is a graph showing the Young's moduli of the TiTaSn example samples of sample Nos. T1 to T7 (final heat treatment temperatures: 25° C., 250° C., 350° C., 450° C., 550° C., 650° C., and 750° C.)
Figure 25:
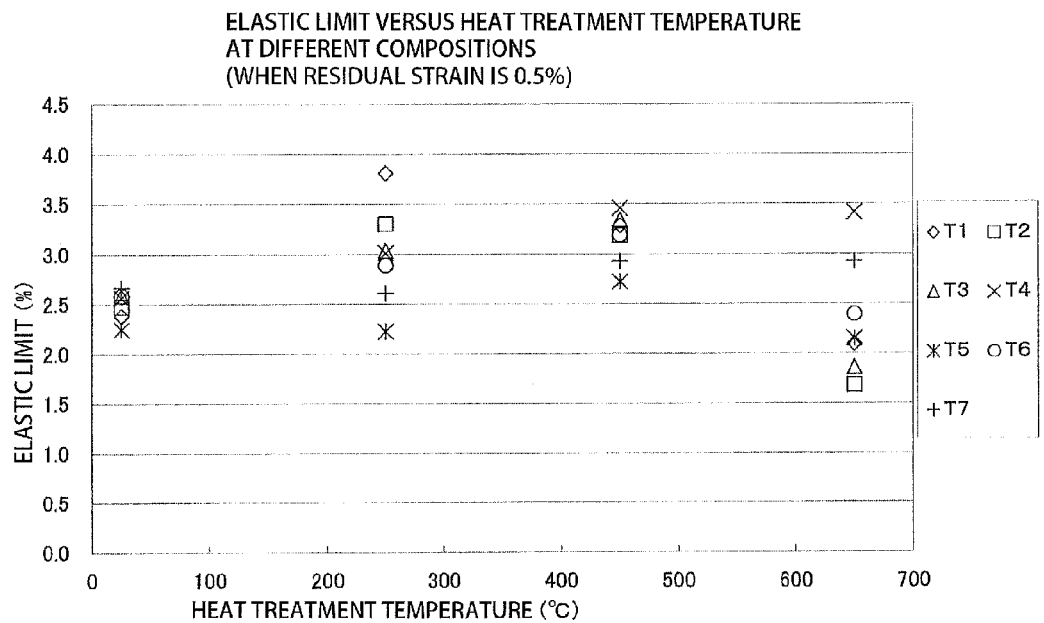
FIG. 25 is a graph showing the elongations with a residual strain of 0.5% (elastic deformation strains, elastic limits) of the TiTaSn example samples of sample Nos. T1 to T7 (final heat treatment temperatures: 25° C., 250° C., 450° C., and 650° C.)

FIG. 22 is a table showing the results of the tensile test, i.e., the values of tensile strength, Young's modulus, and elastic deformation strain (elastic limit), performed on TiTaSn example samples of sample Nos. T1 to T7 (final working rate: 76%). In the figure, the heat treatment temperature of 25° C. means no heat treatment (the same applies to the following). The elastic deformation strain (elastic limit) was not measured for the samples heat-treated at temperatures of 350° C., 550° C., and 750° C. FIGS. 23 to 25 are graphs corresponding to the table in FIG. 22.

FIG. 23 shows a graph (scatter diagram) of the tensile strengths of the TiTaSn example samples of sample Nos. T1 to T7 (final heat treatment temperatures: 25° C., 250° C., 350° C., 450° C., 550° C., 650° C., and 750° C.). As can be seen from the results of the tensile test, it was confirmed that the tensile strength of each of the TiTaSn example samples of sample Nos. T1 to T7 fell within the range of 600 MPa to 1,600 MPa. It was also confirmed that the value of the tensile strength of each of the TiTaSn example samples of sample Nos. T1 to T7 tended to become high when the final heat treatment temperature was about 400 to about 500° C.

FIG. 24 shows a graph (scatter diagram) of the Young's moduli of the TiTaSn example samples of sample Nos. T1 to T7 (final heat treatment temperatures: 25° C., 250° C., 350° C., 450° C., 550° C., 650° C., and 750° C.). As can be seen from the results of the tensile test, it was confirmed that the Young's modulus of each of the TiTaSn example samples of sample Nos. T1 to T7 fell within the range of 25 GPa to 85 GPa. It was also confirmed that the value of the Young's modulus of each of the TiTaSn example samples of sample Nos. T1 to T7 tended to become high when the final heat treatment temperature was about 600 to about 700° C.

FIG. 25 shows a graph (scatter diagram) of the elongations (elastic deformation strains, elastic limits) of the TiTaSn example samples of sample Nos. T1 to T7 (final heat treatment temperatures: 25° C., 250° C., 450° C., and 650° C.) with a residual strain of 0.5%. As can be seen from the results of the tensile test, it was confirmed that the elastic deformation strain (elastic limit) of each of the TiTaSn example samples of sample Nos. T1 to T7 fell within the range of about 1 to about 4% when the final heat treatment temperature was 650° C. or lower. It was also confirmed that the value of the elastic deformation strain (elastic limit) of each of the TiTaSn example samples of sample Nos. T1 to T7 tended to become high when the final heat treatment temperature was about 200 to about 500° C.

Furthermore, on the basis of the results of the tensile test performed on the TiTaSn example samples of sample Nos. T1 to T7 shown in FIG. 22, the relationship between tensile strength and (Ta+Sn)/Ti was examined. In addition, the relationship between the Young's modulus and (Ta+Sn)/Ti and the relationship between the elastic deformation strain (elastic limit) and (Ta+Sn)/Ti were examined. Here, (Ta+Sn)/Ti is the ratio of the total content (at %) of Ta and Sn to the content (at %) of the other components, Ti+unavoidable impurities, i.e., a value obtained by dividing the total atomic % of Ta and Sn by the total atomic % of Ti and unavoidable impurities. In the TiTaSn example samples of sample No. T1, (Ta+Sn)/Ti=(19+4.5)/(100−19−4.5)≅0.31. Similar calculations show the following. In the TiTaSn example samples of sample No. T2, (Ta+Sn)/Ti=0.32. In the TiTaSn example samples of sample No. T3, (Ta+Sn)/Ti≅0.35. In the TiTaSn example samples of sample No. T4, (Ta+Sn)/Ti≅0.38. In the TiTaSn example samples of sample No. T5, (Ta+Sn)/Ti≅0.40. In the TiTaSn example samples of sample No. T6, (Ta+Sn)/Ti≅0.43. In the TiTaSn example samples of sample No. T7, (Ta+Sn)/Ti≅0.46.

Figure 26:
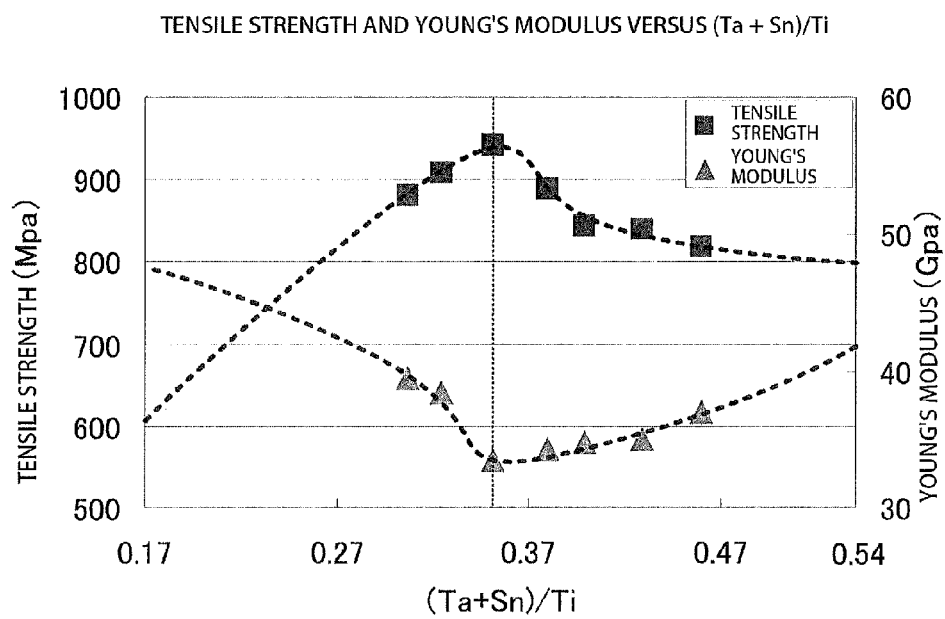
FIG. 26 is a graph showing the relationship between (Ta+Sn)/Ti and tensile strength and the relationship between (Ta+Sn)/Ti and Young's modulus for the TiTaSn example samples of sample Nos. T1 to T7 (final working rate: 76%, no heat treatment).
Figure 27:
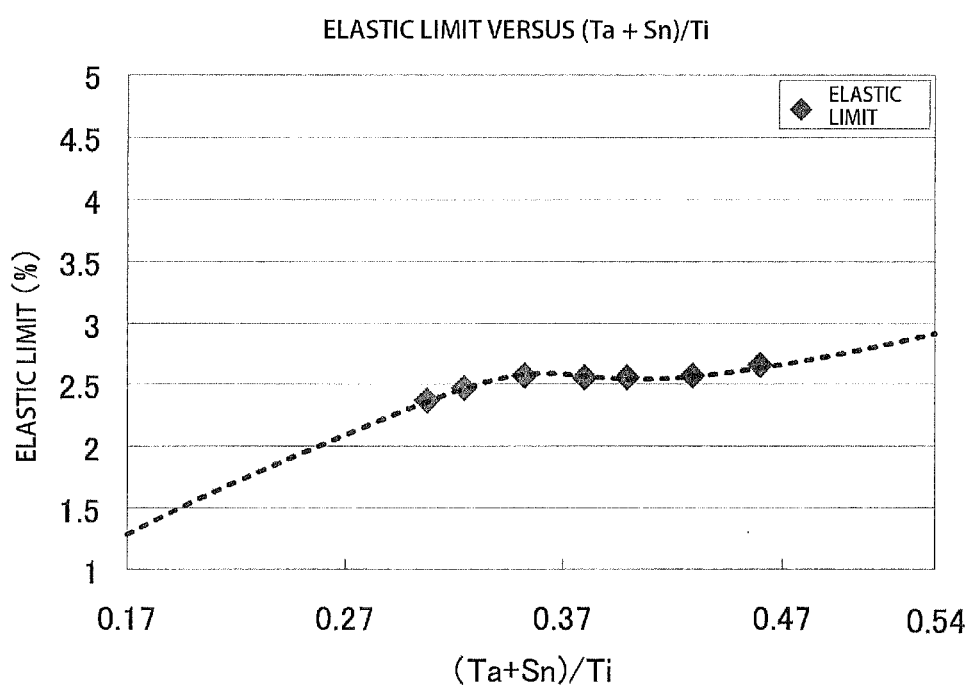
FIG. 27 is a graph showing the relationship between (Ta+Sn)/Ti and elastic deformation strain (elastic limit) for the TiTaSn example samples of sample Nos. T1 to T7 (final working rate: 76%, no heat treatment).

FIG. 26 shows the relationship between (Ta+Sn)/Ti and the tensile strength and the relationship between (Ta+Sn)/Ti and the Young's modulus for TiTaSn example samples of sample Nos. T1 to T7 (final working rate: 76%, no heat treatment). FIG. 27 shows the relationship between (Ta+Sn)/Ti and the elastic deformation strain (elastic limit) for the TiTaSn example samples of sample Nos. T1 to T7 (final working rate: 76%, no heat treatment).

As can be seen from the results of the tensile test on the TiTaSn example samples of sample Nos. T1 to T7 (final working rate: 76%, no heat treatment), it was confirmed that each of the relationship between (Ta+Sn)/Ti and the tensile strength and the relationship between (Ta+Sn)/Ti and the Young's modulus tends to have a peak when the value of (Ta+Sn)/Ti is 0.34 to 0.36 as shown by dashed lines in FIG. 26, and these relationships are similar to each other and axially symmetric. It was confirmed that the relationship between (Ta+Sn)/Ti and the elastic deformation strain (elastic limit) tends to increase steadily from left to right with a peak when the value of (Ta+Sn)/Ti is 0.34 to 0.36 and is substantially similar to the relationship between (Ta+Sn)/Ti and the tensile strength, as shown by a dotted line in FIG. 27.

Therefore, it was confirmed that, when the value of (Ta+Sn)/Ti is 0.17 to 0.54, the tensile strength can be maintained to at least 600 MPa. It was also confirmed that, when the value of (Ta+Sn)/Ti is 0.17 to 0.54, the Young's modulus can be maintained to 50 GPa or lower and the elastic deformation strain (elastic limit) can be maintained to at least 1.0%.

To set the value of (Ta+Sn)/Ti to 0.17 or higher, the total content of Ta and Sn is set to, for example, 15 at % or higher. More specifically, when the total content of Ta and Sn is set to 15 at %, (Ta+Sn)/Ti=15/85≅0.176. Therefore, the basis for limiting the lower limit of the content of Ta to 15 at % or higher and limiting the lower limit of the content of Sn to 0 at % or higher was confirmed from the results of the tensile test. When the content of Ta is 27 at % and the content of Sn is 8 at %, (Ta+Sn)/Ti=(27+8)/65≅0.538.

More specifically, the effectiveness of limiting the upper limit of the content of Ta to 27 at % or lower and limiting the upper limit of the content of Sn to 8 at % or lower was also confirmed from the results of the tensile test.

It was also confirmed that, when the value of (Ta+Sn)/Ti is 0.31 to 0.46, the tensile strength can be about 800 MPa or higher and the Young's modulus can be 40 GPa or lower even without heat treatment and that, when the value of (Ta+Sn)/Ti is 0.32 to 0.38, the tensile strength can be about 880 MPa or higher and the Young's modulus can be 40 GPa or lower even without heat treatment. It was also confirmed that, when the value of (Ta+Sn)/Ti is 0.34 to 0.36, a substantially maximum tensile strength (about 940 MPa) and a substantially minimum Young's modulus (about 34 GPa) can be obtained even without heat treatment.

Therefore, from the viewpoint of obtaining better mechanical properties for medical device materials, biocompatible materials, etc., the value of (Ta+Sn)/Ti is preferably 0.32 to 0.38 and more preferably 0.34 to 0.36. Of course, by appropriately performing heat treatment, still better mechanical properties can be obtained.

As can be seen from the results of the <three-point bending test> and <tensile test> described above, the TiTaSn alloy according to the present invention has high elasticity and appropriate stiffness. Therefore, when the TiTaSn alloy according to the present invention is applied to a medical tool (for example, a stent) for expanding a tubular part of a living body (such as a blood vessel, a trachea, an esophagus, a duodenum, a large intestine, a small intestine, or a biliary tract) from its interior, a large area of contact with the inner wall of the tubular part can be ensured, and the inner wall of the tubular part can be appropriately supported, so that restenosis can be effectively prevented.

In addition, when the TiTaSn alloy according to the present invention is applied to a medical tool (such as a medical guidewire, a medical delivery wire, a medical stent, a medical clip, an aneurysm embolization coil or a vein filter, or a dental cleanser, a dental reamer, a dental file or an orthodontic wire) that is inserted into a tubular part of a living body and moved along a complicated path, the medical tool can be moved smoothly, and the inner wall of the tubular part is less likely to be damaged.

INDUSTRIAL APPLICABILITY

The titanium alloy according to the present invention can be used for medical guidewires, medical delivery wires, medical stents, medical clips, aneurysm embolization coils or vein filters, or dental cleansers, dental reamers, dental files or orthodontic wires, etc.

The invention claimed is:

1. A titanium alloy for a living body, consisting of:
    15 to 27 atomic % (at %) of tantalum (Ta); and
    1 to 8 at % of tin (Sn) with the balance being titanium (Ti) and unavoidable impurities, when an entire amount of the titanium alloy is taken as 100 at %;
    wherein the titanium alloy has a Young's modulus of 40 Gpa or lower and a tensile strength of 800 MPa or larger and a value obtained by dividing the total atomic % of the tantalum and the tin by the total atomic % of the titanium and the unavoidable impurities is within a range of 0.34 to 0.36 within which the titanium alloy has both at once a maximum tensile strength and a minimum Young's modulus.

2. The titanium alloy according to claim 1, wherein a saturation magnetic flux density in a B-H curve obtained by a VSM method is $5.0 \times 10^{-4}$ T (tesla) or lower when a strength of a magnetic field is $4.0 \times 10^5$ A/m.

3. The titanium alloy according to claim 1, having an elastic deformation strain of 1.0% or larger.

4. The titanium alloy according to claim 1, wherein in a three-point bending test performed under measurement conditions in which a distance between two supporting members is 20 mm and a diameter d of a pointed end of each of the supporting members and a pressing member is 5 mm, when the pressing member presses the titanium alloy formed into a wire having a diameter φ of 0.5 mm to a pressing depth of 4 mm at a pressing rate of 1 mm/minute and then a load is released, an amount of recovery of the wire is 60% or higher.

5. The titanium alloy according to claim 1, wherein a degree of cell injury when a metal ion concentration measured by ICP emission spectrometry is 64 ppm or less is less than 10%.

6. The titanium alloy according to claim 1, wherein the titanium alloy is formed into a medical guidewire, a medical delivery wire, a medical stent, a medical clip, an aneurysm embolization coil or a vein filter, or a dental cleanser, a dental reamer, a dental file or an orthodontic wire.

7. The titanium alloy according to claim 6, having a maximum outer diameter of 0.005 mm to 1 mm.

8. The titanium alloy according to claim 1, wherein the tantalum content is 22 to 24 at %.

* * * * *